United States Patent

Ogihara et al.

[11] Patent Number: 5,659,059
[45] Date of Patent: Aug. 19, 1997

[54] SILACYCLOHEXANE COMPOUND, A METHOD OF PREPARING IT AND A LIQUID CRYSTAL COMPOSITION CONTAINING IT

[75] Inventors: Tsutomu Ogihara; Takaaki Shimizu; Takeshi Kinsho; Tatsushi Kaneko; Ryuichi Saito, all of Kubika-mura; Hideshi Kurihara, Kawasaki, all of Japan

[73] Assignee: Shin-Etsu Chemical Co., Ltd., Tokyo, Japan

[21] Appl. No.: 331,957

[22] Filed: Oct. 31, 1994

[30] Foreign Application Priority Data

Nov. 1, 1993 [JP] Japan .................................. 5-296082

[51] Int. Cl.$^6$ ........................................................ C07F 7/08
[52] U.S. Cl. .................. 556/406; 252/299.6; 252/299.63
[58] Field of Search .................... 556/406; 252/299.6, 252/299.63

[56] References Cited

U.S. PATENT DOCUMENTS 4,826,984  5/1989  Berlin et al. .................... 556/406 X
4,973,723  11/1990  Cawthon et al. ................ 556/406

Primary Examiner—Paul F. Shaver
Attorney, Agent, or Firm—Townsend & Banta

[57] ABSTRACT

A silacyclohexane compound represented by the following general formula (I).

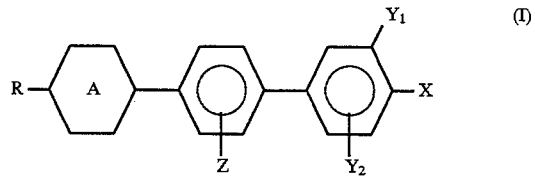

In this formula, R denotes a linear-chain alkyl group with a carbon number of 1–10, a mono- or di- fluoro-alkyl group with a carbon number of 1–10, a branched-chain alkyl group with a carbon number of 3–8, an alkoxyalkyl group with a carbon number of 2–7, or an alkenyl group with a carbon number of 2–8.

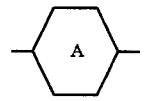

denotes trans-1-sila-1,4-cyclohexylene or trans-4-sila-1,4-cyclohexylene group whose silicon at position 1 or position 4 has a substitutional group(s) of H, F, Cl or CH$_3$. X denotes a CN, F, Cl, CF$_3$, CF$_2$Cl, CHFCl, OCF$_3$, OCHF$_2$, OCF$_2$Cl, OCHFCl, R or OR group (R is the same as defined in the general formula (I)). Y$_2$ and Z denote H or F, independently to each other. Y$_1$ denotes H, F or Cl.

6 Claims, No Drawings

SILACYCLOHEXANE COMPOUND, A METHOD OF PREPARING IT AND A LIQUID CRYSTAL COMPOSITION CONTAINING IT

BACKGROUND OF THE INVENTION

1. Field of the Invention

This invention relates to a new silacyclohexane compound, a method of preparing it, and a liquid crystal composition which contains it as well as a liquid crystal display element which contains said liquid crystal composition.

2. The Prior Art

A liquid crystal display element utilizes the optical anisotropy and dielectric anisotropy of liquid crystal substances. Display methods include the TN mode (twisted nematic mode), the STN mode (super twisted nematic mode), the SBE mode (super birefringence mode), the DS mode (dynamic scattering mode), the guest-host mode, the DAP mode ("deformation of aligned phase" mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability against moisture, air, light, heat, electric fields, etc., are commonly required in all display methods. Furthermore, it is desirable for the liquid crystal material to have a low viscosity, and also to have a short address time, low threshold voltage and high contrast in the cell(s).

Currently, there is no single compound which satisfies all of these requirements. In practice, liquid crystal mixtures are obtained by mixing several to more than ten liquid crystal compounds and latent liquid crystal compounds. Because of this, it is also important that components of a liquid crystal composition mix easily.

Among liquid crystal compounds which can be components for these, one of the basic components conventionally known which controls the electro-optical performance is a compound which has a so-called cyclohexyl ring-phenyl ring-phenyl ring structure (BCH structure) such as

(Japanese examined patent publication (Tokko) Sho 63-55496),

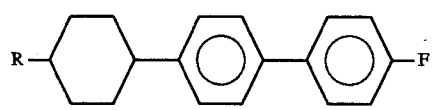

(Tokko Sho 63-7169) and

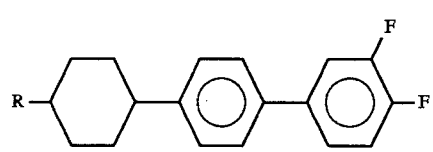

(Tokko Hei 64-4496).

In recent years, along with the expansion of the applications of liquid crystal displays, the characteristics required of liquid crystal materials are becoming more and more advanced and demanding. In particular, superior characteristics such as improved low temperature performance, a wider temperature range for automobile onboard use and a lower driving voltage, compared with conventional liquid crystal substances, are desired.

BRIEF SUMMARY OF THE INVENTION

From such a viewpoint, this invention is a newly developed liquid crystal substance targeting improvement in characteristics of liquid crystal substances, and its object is to provide a liquid crystal compound containing silacyclohexane rings, which is completely different from the conventional liquid crystal compounds with cyclohexyl ring-phenyl ring-phenyl ring structures (BCH structures).

That is, this invention is a silacyclohexane compound represented by the following general formula (I):

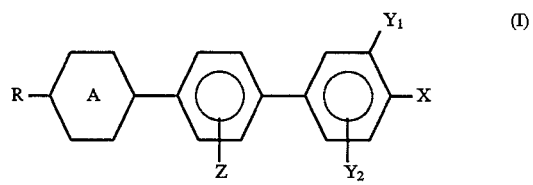

In this formula, R denotes a linear-chain alkyl group with a carbon number of 1–10, a mono- or di- fluoro-alkyl group with a carbon number of 1–10, a branched-chain alkyl group with a carbon number of 3–8, an alkoxyalkyl group with a carbon number of 2–7, or an alkenyl group with a carbon number of 2–8.

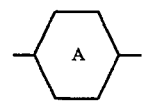

denotes trans-1-sila-1,4-cyclohexylene or trans-4-sila-1,4-cyclohexylene group whose silicon at position 1 or position 4 has a substitutional group(s) of H, F, Cl or $CH_3$.

X denotes a CN, F, Cl, $CF_3$, $CF_2Cl$, $CHFCl$, $OCF_3$, $OCHF_2$, $OCF_2Cl$, $OCHFCl$, R or OR group (R is the same as defined in the general formula (I)). $Y_2$ and Z denote H or F, independently to each other. $Y_1$ denotes H, F or Cl.

This invention is also a method of preparing the silacyclohexane compound as represented by the general formula (I) characterized by carbon—carbon bond formation or carbon-silicon bond formation using a specific organometallic reagent. The preparation methods are listed below.

A method of preparing the silacyclohexane compound as represented by said general formula (I) which uses a reaction between an organometallic reagent R-M (M denotes MgP, ZnP (P denotes a halogen atom) or Li) and a silacyclohexane compound

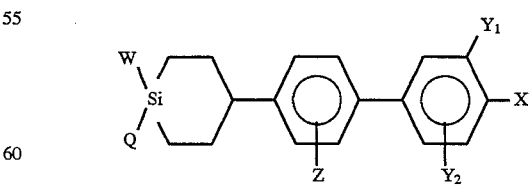

(where, W denotes a H, F, Cl or CH3 group, Q denotes a halogen or alkoxy group, and X, $Y_1$, $Y_2$ and Z are the same as defined in the general formula (I)).

A method of preparing the silacyclohexane compound as represented by said general formula (I) which uses a reaction between an organometallic reagent

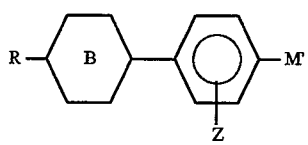

(R and Z are the same as defined in the general formula (I), M' denotes M or B(OR')$_2$ (R' denotes a Me group or a H atom), and

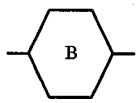

denotes trans-1-sila-1,4-cyclohexylene or trans-4-sila-1,4-cyclohexylene group whose silicon at position 1 or position 4 has a substitutional group(s) of H or CH$_3$) and an aromatic compound

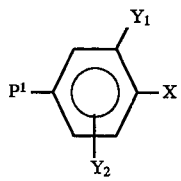

(P$^1$ denotes Cl, Br or I, and X, Y$_1$ and Y$_2$ are the same as defined in the general formula (I)).

A method of preparing the silacyclohexane compound as represented by said general formula (I) which uses a reaction between an organometallic reagent

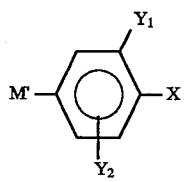

(X, Y$_1$ and Y$_2$ are the same as defined in the general formula (I), and M' is the same as defined before.) and a silacyclohexane compound

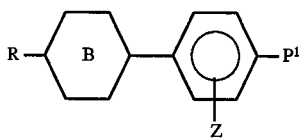

(R and Z are the same as defined in the general formula (I), P$^1$ and

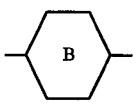

are the same as defined before.)

A method of preparing the silacyclohexane compound which uses a reaction between a silacyclohexane compound

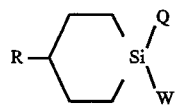

(R is the same as defined in the general formula (I), and W and Q are the same as defined before) and an organometallic reagent

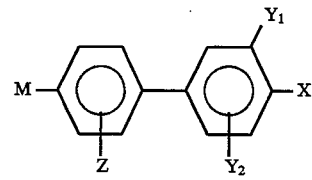

(X, Y$_1$, Y$_2$ and Z are the same as defined in the general formula (I), and M denotes MgP, ZnP (P denotes a halogen atom) or Li).

Furthermore, this invention is a liquid crystal composition characterized by containing the compound represented by the general formula (I) described above and a liquid crystal display element which uses this composition.

DETAILED DESCRIPTION

The new compounds represented by the general formula (I) are silacyclohexane compounds specifically represented by a ring structure shown below:

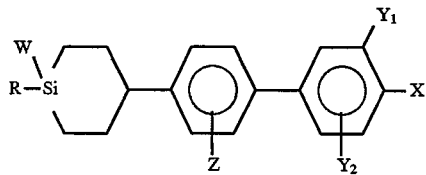

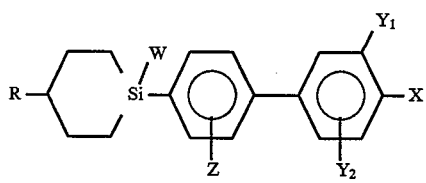

In these formulas, R denotes: a linear-chain alkyl group with a carbon number of 1–10, i.e. a methyl, ethyl, n-propyl, n-butyl, n-pentyl, n-hexyl, n-heptyl, n-octyl, n-nonyl or n-decyl group; a mono- or di- fluoro-alkyl group with a carbon number of 1–10, i.e. a fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1- difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl or 10,10-difluorodecyl group; a branched-chain alkyl group with a carbon number of 3–8, i.e. isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group; or an alkoxyalkyl group with a carbon number of 2–7, i.e. a methoxymethyl, ethoxymethyl, propoxymethyl, butoxymethyl, pentoxymethyl, methoxyethyl, ethoxyethyl, propoxyethyl, butoxyethyl, methoxypropyl, ethoxypropyl, propoxypropyl, methoxybutyl, ethoxybutyl, methoxypentyl or ethoxypentyl group; or an alkenyl group with a carbon number of 2–8, i.e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group.

W denotes H, F, Cl or $C_3$. X denotes CN, F, Cl, $CF_3$, $CF_2Cl$, $CHFCl$, $OCF_3$, $OCHF_2$, $OCF_2Cl$, $OCHFCl$, R or OR. $Y_2$ and Z denote H or F, independently to each other. $Y_1$ denotes H, F or Cl.

Specific examples of

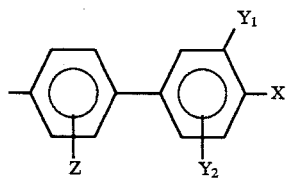

follow:

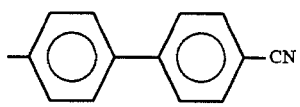

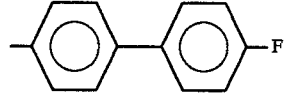

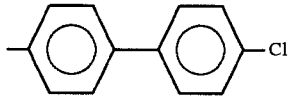

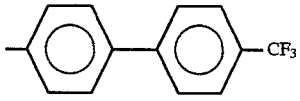

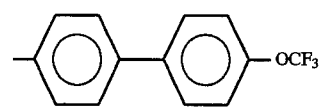

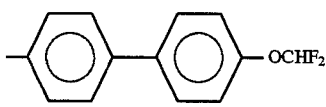

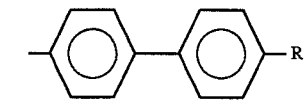

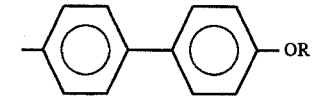

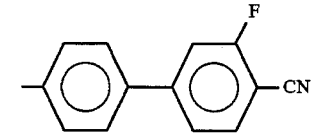

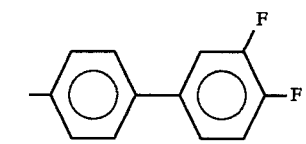

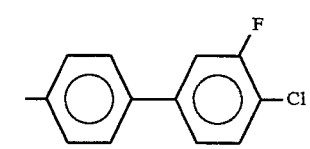

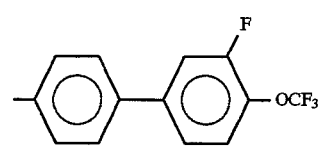

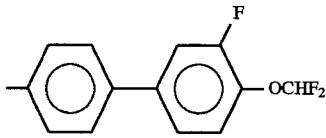

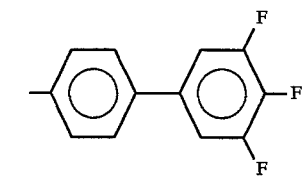

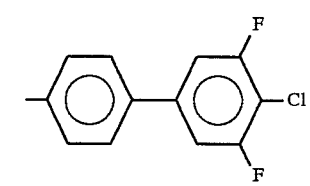

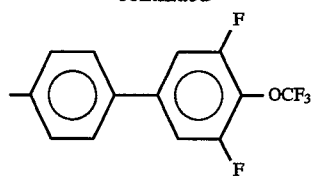
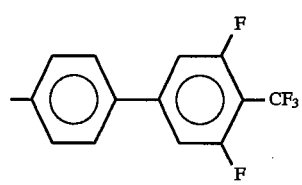
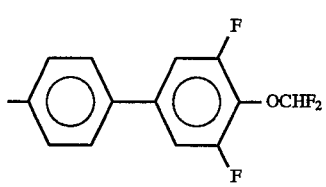
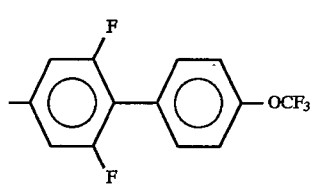
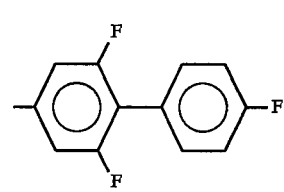
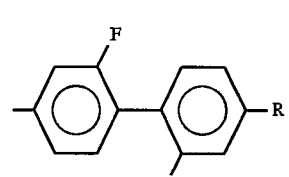
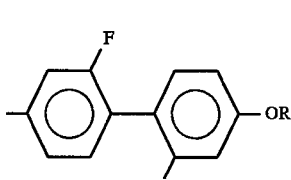
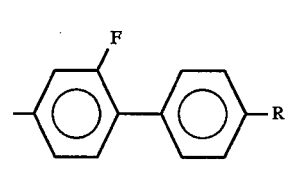
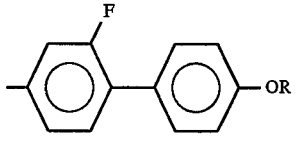
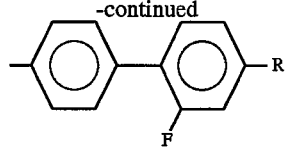
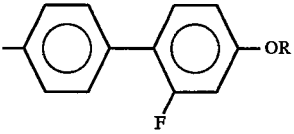
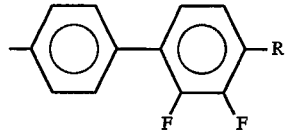
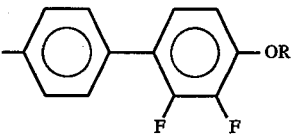
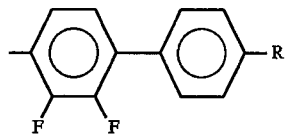
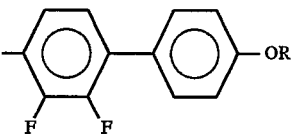
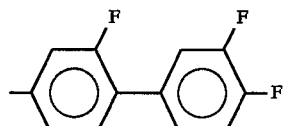
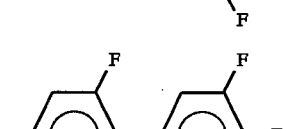
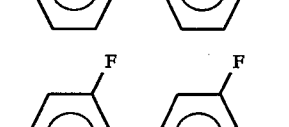
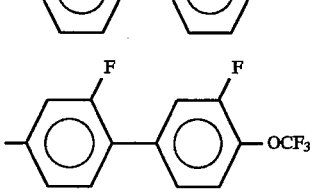
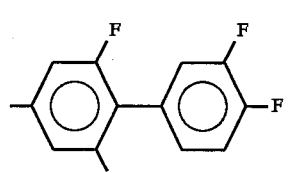

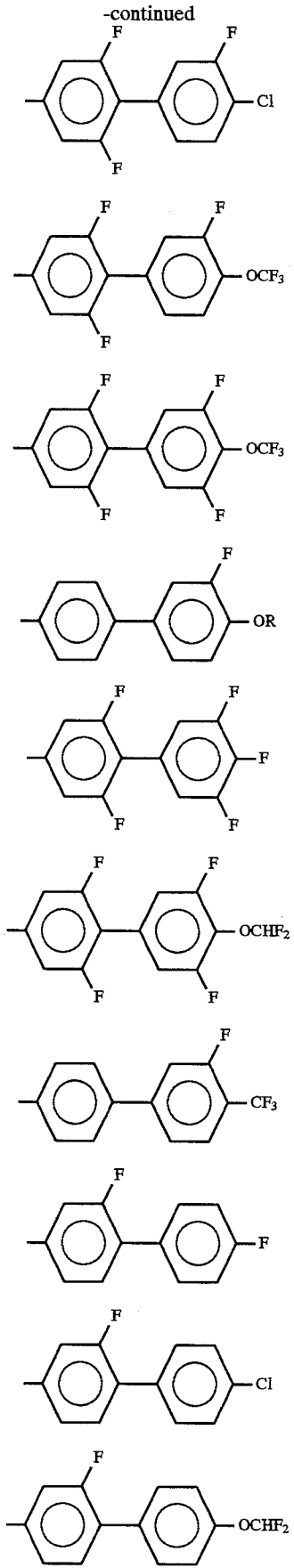

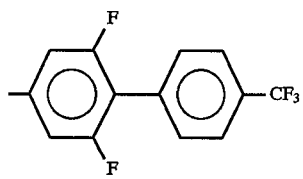 5

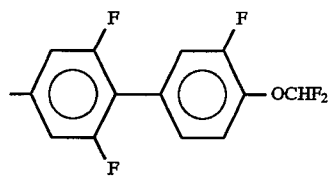 10

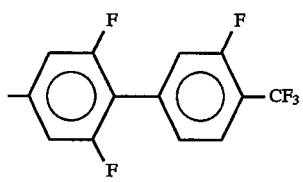 20

For R, the following groups are desirable for practical use: a linear-chain alkyl group with a carbon number of 3–7, i.e. a n-propyl, n-butyl, n-pentyl, n-hexyl or n-heptyl group, some mono- or di- fluoro alkyl groups including 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fhorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4 -difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl groups, some branched-chain alkyl groups including isopropyl, 1-methylpropyl, 2-methylpropyl, 1-methylbutyl, 2-methylbutyl, 3-methylbutyl, 1-methylpentyl, 2-methylpentyl and 2-ethylhexyl groups, an alkoxyalkyl group with a carbon number of 2–6, i.e. a methoxymethyl, methoxyethyl, methoxypropyl, methoxypentyl, ethoxymethyl, ethoxyethyl, propoxymethyl or pentoxymethyl group, or some alkenyl groups including vinyl, 1-propenyl, 3-butenyl, 1-pentenyl, 3-pentenyl, 4-pentenyl, 1-hexenyl, 5-hexenyl, 6-heptenyl and 7-octenyl group.

H, F and $CH_3$ groups are desirable for W in practical use. F, Cl, Br, I, $OCH_3$ and $OC_2H_5$ are preferable for Q.

Groups desirable in practical use for

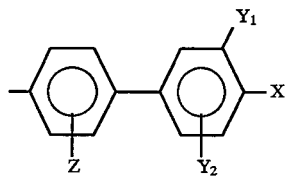 55 are

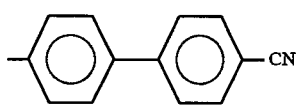

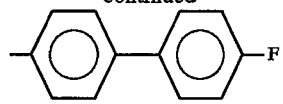

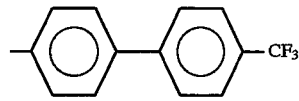

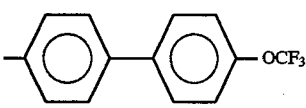

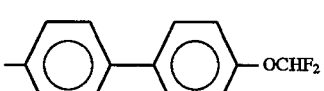

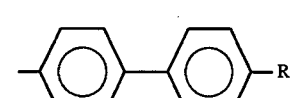

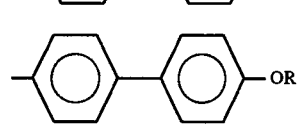

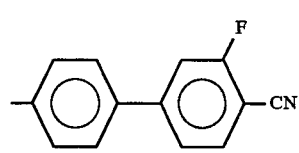

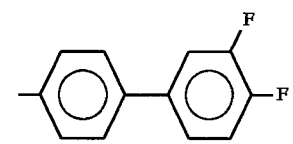

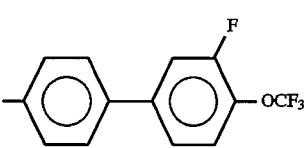

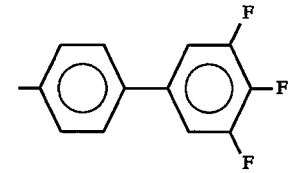

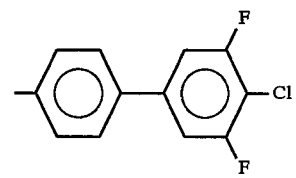

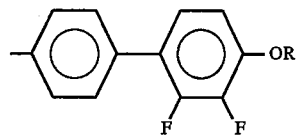

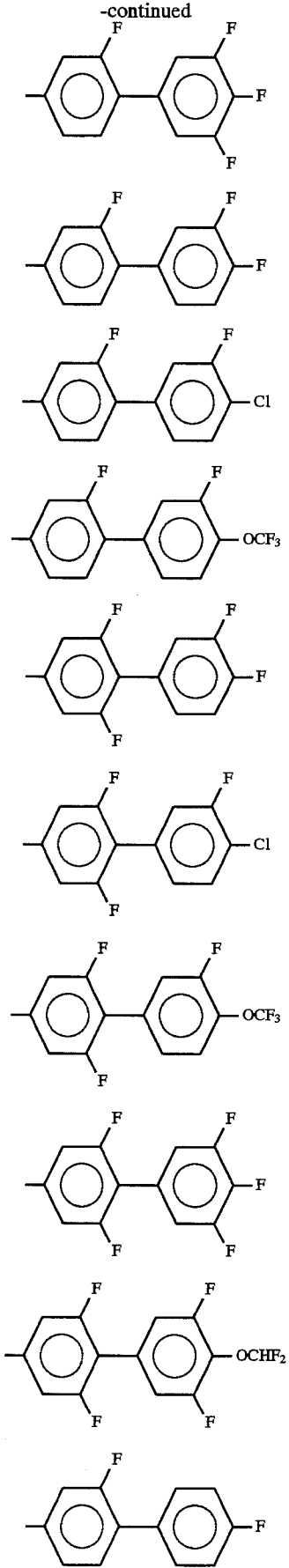
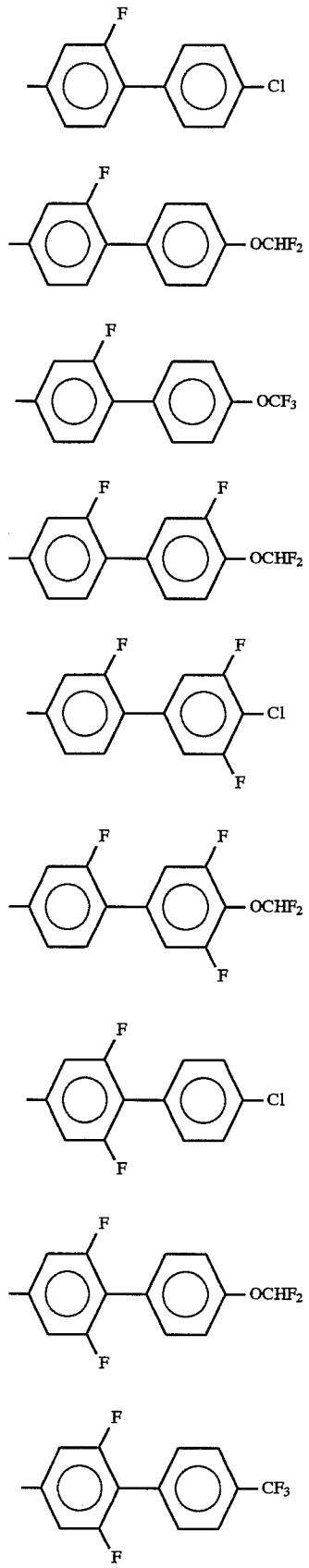

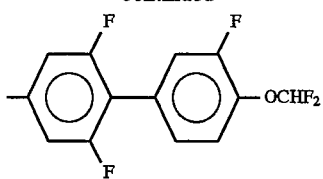
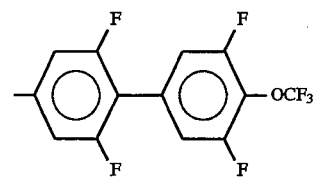
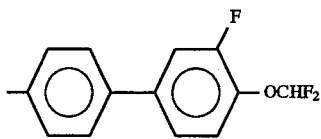
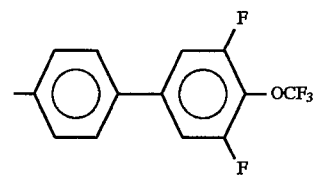
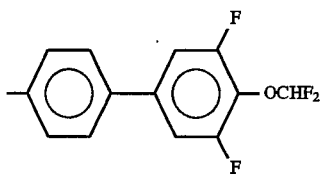
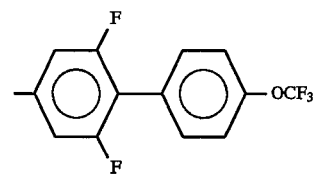
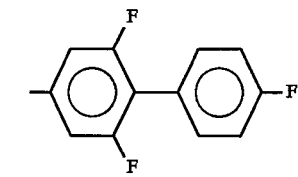
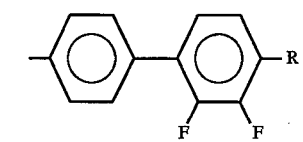
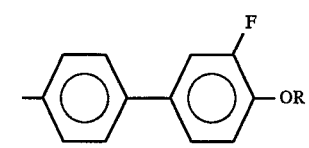
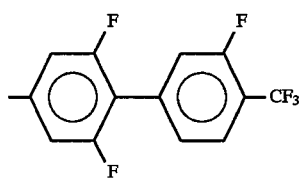
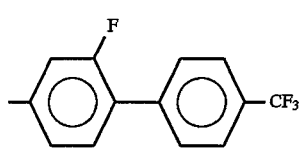
A method of preparing these compounds is described below. Although the reaction substrates are somewhat different depending on the ring structure, all of them are prepared using the organometallic reagent coupling reactions (A)–(D) shown below.
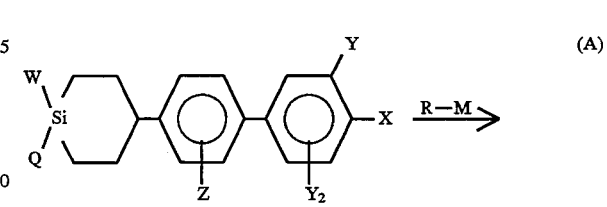
(A)
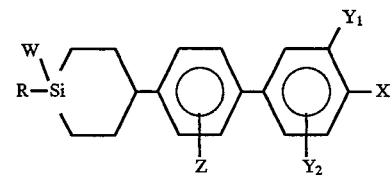
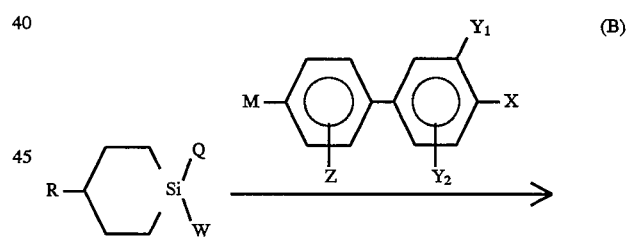
(B)
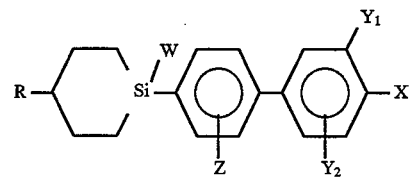
(C)

-continued

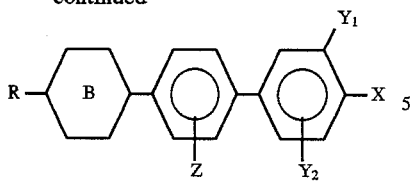

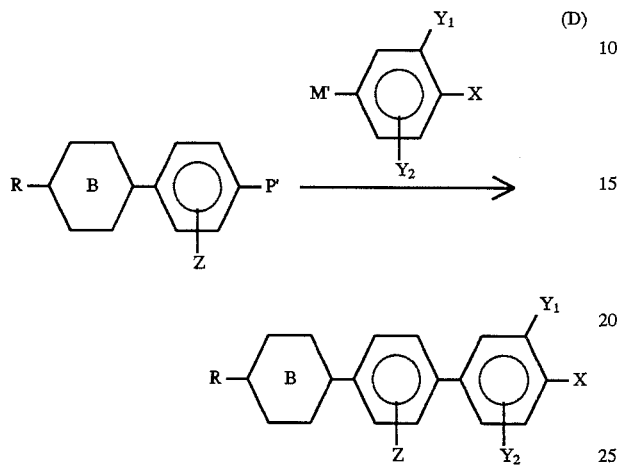

In the preparation method described above, a R-halide, aromatic halide or silacyclohexyl halide is brought into reaction with a metal in a solvent to obtain an organometallic reagent. For example, in the coupling reaction (C), the organometallic reagent

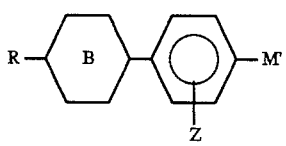

(P and P' denote halogen atoms.)

can be easily prepared from the corresponding halide

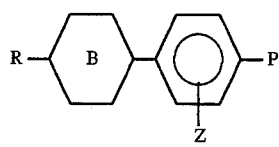

(P denotes a halogen atom). For example, the reaction path shown below can be used.

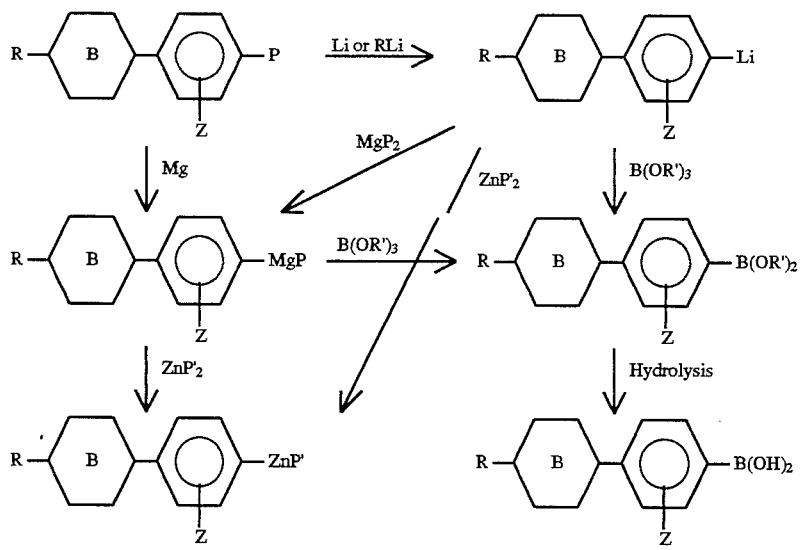

It is also possible to directly ortho-lithiate

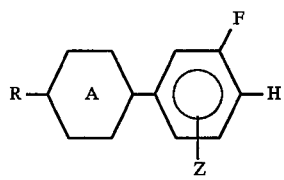

by using a reaction with alkyl lithium, thus synthesize a compound

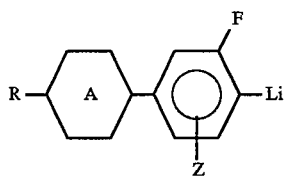

and then follow the synthesis path described above.

Similarly, as for the coupling reaction (D), by replacing

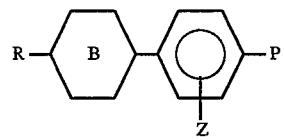

with

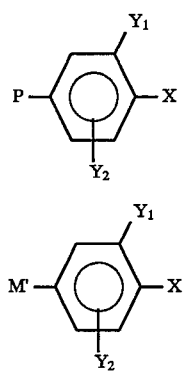

can be obtained.

For the solvent used in this, ether solvents such as diethylether and THF (tetrahydrofuran) and hydrocarbon solvents such as toluene and xylene can be used independently or in combination. The appropriate metal is chosen depending on the type of the substitutional groups X, Y, P and $P^1$. P and $P^1$ are preferably Cl, Br or I.

The organometallic reagent thus generated is then brought into reaction with a silacyclohexane compound whose silicon has substitutional groups W and Q, as shown in the coupling reactions (A) and (B), or with an aromatic halide, as shown in the coupling reactions (C) and (D).

The coupling reactions (C) and (D) require a heavy metal catalyst. Particularly preferable are palladium and nickel catalysts. Examples of the nickel catalysts are (1,3-bis (diphenylphosphino) propane) nickel chloride (II), (1,2-bis (diphenylphosphino) ethane) nickel chloride (II) and bis (triphenylphosphine) nickel chloride (II). Examples of the palladium catalysts are tetrakis (triphenylphosphine) palladium (0), bis (1,2-bis (diphenylphosphino) ethane) palladium (0) and bis (dibenzylideneacetone) palladium (0).

The compound produced here is a mixture of trans isomers and cis isomers in terms of the conformation of the silacyclohexane ring. A conventional purification means such as chromatography and recrystallization is employed to separate and purify the trans isomers to obtain the silacyclohexane compound of this invention represented by the general formula (I).

The silacyclohexane compound of this invention can be mixed with known compounds to obtain a liquid crystal composition. The compound used for mixing to obtain the liquid crystals compound can be chosen from among the known compounds shown below.

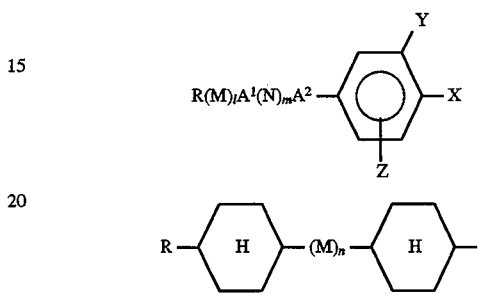

In the above general formulas, (M) and (N) each denote one of the following:

1) A trans-1,4-cyclohexylene group which has no substitution or which has one or more substitutional groups from among F, Cl, Br, CN and alkyl groups, 2) A ring comprising a cyclohexane ring in which O or S is substituted for one or nonadjacent two $CH_2$ groups, 3) A 1,4-cyclohexenylene group, 4) A 1,4-phenylene group which has no substitution or which has one or two substitutional groups from among F, Cl, $CH_3$ and CN groups, or 5) A ring comprising a 1,4-phenylene group in which an N atom is substituted for one or two CH groups.

$A^1$ and $A^2$ denote $—CH_2CH_2—$, $—CH=CH—$, $—C\equiv C—$, $—CO_2—$, $—OCO—$, $—CH_2O—$, $—OCH_2—$ or a single bond.

l, m=0, 1 or 2 (where l+m=1, 2 or 3, and n=0, 1 or 2)

R denotes a linear-chain alkyl group with a carbon number of 1–10, a mono- or di-fluoro-alkyl group with a carbon number of 1–10, a branched-chain alkyl group with a carbon number of 3–8, an alkoxyalkyl group with a carbon number of 2–7, or an alkenyl group with a carbon number of 2–8.

X, Y and Z are the same as defined for the general formula (I).

In the above description, if l or n=2, then (M) can contain heterogeneous rings, and if m=2, then (N) can contain heterogeneous rings.

The ratio of one or more types of the silacyclohexane compound of this invention contained in the liquid crystal composition is 1–50 wt %, more preferably 5–30 wt %. The liquid crystal composition can also contain a polygenetic dye(s) to generate a colored guest-host system and additives to change the dielectric anisotropy, viscosity and the orientation of the nematic phase.

The liquid crystal composition thus formed can be used to manufacture various liquid crystal display elements in conventional methods. That is, the liquid crystal composition containing the silacyclohexane compound of this invention is sealed between transparent plates which have electrodes of desired shapes and is thus used as liquid crystal display elements. This element can have various undercoatings, overcoatings for orientation control, a polarizer plate(s), a filter(s) and a reflector layer(s), as necessary. It can be made into a laminated cell or combined with other display elements. Semiconductor substrates and light sources can also be used to make various types of displays.

For the driving method of the liquid crystal display element, prior-art methods in the industry of liquid crystal display elements such as the dynamic scattering (DSM) method, the twisted nematic (TN) method, the guest-host (GH) method and the super twisted nematic (STN) method can be adopted.

EXAMPLES

The details of this invention are described below by referring to specific examples.

[Example 1]

(Preparation of 4'-(trans-4-n-propyl-4-silacyclohexyl)-4-fluorobiphenyl)

2.5 g (20 mmol) of n-propyl bromide was dripped into a mixture of 0.5 g of magnesium (21 mmol) and 50 ml of tetrahydrofuran (hereafter abbreviated as "THF") to obtain a Grignard's reagent. This solution was then dripped into a 50 ml THF solution of 6.1 g (20 mmol) of 4'-(4-chloro-4-silacyclohexyl)-4-fluorobiphenyl to obtain 4'-(trans-4-n-propyl-4-silacyclohexyl)-4-fluorobiphenyl.

The silacyclohexane rings of this product were a mixture of trans and cis isomers. They were separated by means of chromatography to obtain 5.7 g of the trans isomer (yield 91%). The results of its analysis are shown below.

IR (liquid film) νmax: 2918, 2854, 2087, 1604, 1497, 1238, 987, 889 and 816 $cm^{-1}$.

C-N transition temperature: 80.2° C.,

N-I transition temperature: 119.3° C.

[Example 2]

(Preparation of 4'-(trans-4-(1-propenyl)-4-silacyclohexyl)-4-n-propylbiphenyl)

Preparation was conducted in the same manner as in Example 1 except for the fact that allyl chloride was used instead of n-propylbromide and that 4'-(4-chloro-4-silacyclohexyl)-4-n-propylbiphenyl was used instead of 4'-(4-chloro-4-silacyclohexyl)- 4-fluorobiphenyl.

[Example 3]

(Preparation of 4'-(trans-4-isobutyl-4-silacyclohexyl)-4-difluoromethoxybiphenyl)

Preparation was conducted in the same manner as in Example 1 except for the fact that isobutyl bromide was used instead of n-propylbromide and that 4'-(4-chloro-4-silacyclohexyl)-4-difluoromethoxybiphenyl was used instead of 4'-(4-chloro-4-silacyclohexyl)-4-fluorobiphenyl.

[Example 4]

(Preparation of 4'-(trans-4-n-propyl-4-silacyclohexyl)-3,4,5-trifluorobiphenyl)

2.5 g (20 mmol) of n-propyl bromide was dripped into a mixture of 0.5 g of magnesium (21 mmol) and 50 ml of THF to obtain a Grignard's reagent. This solution was then dripped into a 50 ml THF solution of 6.5 g (20 mmol) of 4'-(4-fluoro-4-silacyclohexyl)-3,4,5-trifluorobiphenyl to obtain 4'-(trans-4-n-propyl-4-silacyclohexyl)-3,4,5-trifluorobiphenyl. The silacyclohexane rings of this product were a mixture of trans and cis isomers. They were separated by means of chromatography to obtain 5.9 g of the trans isomer (yield 91%).

[Example 5]

(Preparation of 4'-(trans-4-n-pentyl-4-fluoro-4-silacyclohexyl)-4-trifluoromethylbiphenyl)

3.0 g (20 mmol) of n-pentyl bromide was dripped into a mixture of 0.5 g of magnesium (21 mmol) and 50 ml of THF to obtain a Grignard's reagent. This solution was then dripped into a 50 ml THF solution of 7.1 g (20 mmol) of 4'-(4,4-difluoro-4-silacyclohexyl)-4-trifluoromethylbiphenyl to obtain 4'-(trans-4-n-pentyl-4-fluoro-4-silacyclohexyl)-4-trifluoromethylbiphenyl. The silacyclohexane rings of this product were a mixture of trans and cis isomers. They were separated by means of chromatography to obtain 6.4 g of the trans isomer (yield 78%).

[Example 6]

(Preparation of 4'-(trans-4-n-butyl-4-methyl-4-silacyclohexyl)-4-chloro-3,5-difluorobiphenyl)

A 12.5 ml hexane solution of 1.6M butyl lithium was dripped into a 50 ml THF solution of 7.3 g (20 mmol) of 4'-(4-chloro-4-methyl-4-silacyclohexyl)-4-chloro-3,5-difluorobiphenyl to obtain 4'-(trans-4-n-butyl-4-methyl-4-silacyclohexyl)-4-chloro-3,5-difluorobiphenyl. The silacyclohexane rings of this product were a mixture of trans and cis isomers. They were separated by means of chromatography to obtain 6.6 g of the trans isomer (yield 87%).

[Example 7]

(Preparation of 4'-(trans-4-n-pentyl-4-silacyclohexyl)-2,2'-difluoro-4-propoxybiphenyl)

3.0 g (20 mmol) of n-pentyl bromide was dripped into a mixture of 0.5 g of magnesium (21 mmol) and 50 ml of THF to obtain a Grignard's reagent. This solution was then dripped into a 50 ml THF solution of 7.5 g (20 mmol) of 4'-(4-methoxy-4-silacyclohexyl)-2,2'-difluoro-4-propoxybiphenyl to obtain 4'-(trans-4-n-pentyl-4-silacyclohexyl)-2, 2'-difluoro-4-propoxybiphenyl. The silacyclohexane rings of this product were a mixture of trans and cis isomers. They were separated by means of chromatography to obtain 7.1 g of the trans isomer (yield 86%).

[Example 8]

(Preparation of 4'-(trans-4-n-pentyl-4-silacyclohexyl)-2',5'-difluoro-4-trifluoromethoxybiphenyl)

3.0 g (20 mmol) of n-pentyl bromide was dripped into a mixture of 0.5 g of magnesium (21 mmol) and 50 ml of THF to obtain a Grignard's reagent. This solution was then dripped into a 50 ml THF solution of 8.8 g (20 mmol) of 4'-(4-ethoxy-4-silacyclohexyl)-2',5'-difluoro-4-trifluoromethoxybiphenyl to obtain 4'-(trans-4-n-pentyl-4-silacyclohexyl)-2',5'-difluoro-4-trifluoromethoxybiphenyl. The silacyclohexane rings of this product were a mixture of trans and cis isomers. They were separated by means of chromatography to obtain 7.5 g of the trans isomer (yield 85%).

[Example 9]

(Preparation of 4'-(trans-4-n-pentyl-4-methyl-4-silacyclohexyl)-2'-fluoro-4-propylbiphenyl)

7.1 g (20 mmol) of 4-(trans-4-n-pentyl-4-methyl-4-silacyclohexyl)-1-bromo-2-fluorobenzene was dripped into a mixture of 0.5 g of magnesium (21 mmol) and 50 ml of THF to obtain a Grignard's reagent. This solution was then dripped into a 50 ml THF solution of 4.0 g (20 mmol) of p-propylbromobenzene and a catalytic amount of tetrakis (triphenylphosphine) palladium (0) to obtain 4'-(trans-4-n-pentyl-4-methyl-4-silacyclohexyl)-2'-fluoro-4-propylbiphenyl. This was then purified by means of chromatography to obtain 7.2 g of the target product (yield 91%).

[Example 10]

(Preparation of 4'-(trans-4-(1-propenyl)-4-silacyclohexyl)-3-fluoro-4-trifluoromethoxybiphenyl)

5.6 g (20 mmol) of p-(trans-4-(1-propenyl)-4-silacyclohexyl) chlorobenzene was dripped into a mixture of 0.5 g of magnesium (21 mmol) and 50 ml of THF to obtain a Grignard's reagent. This solution was then dripped into a 50 ml THF solution of 4.3 g (20 mmol) of 1-chloro-4-trifluoromethoxy-3-fluorobenzene and a catalytic amount of (1,3-bis (diphenylphosphino) propane) nickel chloride (II) to obtain 4'-(trans-4-(1-propenyl)-4-silacyclohexyl)-3-fluoro-4-trifluoromethoxybiphenyl. This was then purified by means of chromatography to obtain 7.4 g of the target product (yield 94%).

[Example 11]

(Preparation of 4'-(trans-4-n-pentyl-4-silacyclohexyl)-4-trifluoromethoxybiphenyl)

6.5 g (20 mmol) of p-(trans-4-n-pentyl-4-silacyclohexyl) bromobenzene was dripped into a mixture of 0.5 g of magnesium (21 mmol) and 50 ml of THF to obtain a Grignard's reagent. This solution was then dripped into a THF solution of 2.1 g trimethyl borate, and a boric acid derivative was obtained by means of hydrolysis by acid. This solution was then dripped into a 50 ml THF solution of 4.8 g (20 mmol) of p-trifluoromethoxybromobenzene and a catalytic amount of tetrakis (triphenylphosphine) palladium (0) to obtain 4'-(trans-4-n-pentyl-4-silacyclohexyl)-4-trifluoromethoxybiphenyl. This was then purified by means of chromatography to obtain 7.4 g of the target product (yield 91%). The results of its analysis are shown below.

C-S transition temperature: 68.3° C.,
S-N transition temperature: 103.1° C.,
N-I transition temperature: 113.9° C.

[Example 12]

(Preparation of 4'-(trans-4-n-pentyl-4-silacyclohexyl)-2-fluoro-4-methoxybiphenyl)

6.5 g (20 mmol) of p-(trans-4-n-pentyl-4-silacyclohexyl) bromobenzene was dripped into a mixture of 0.5 g of magnesium (21 mmol) and 50 ml of THF to obtain a Grignard's reagent. This solution was then dripped into a 50 ml THF solution of 5.0 g (20 mmol) of 2-fluoro-1-iodo-4-methoxybenzene and a catalytic amount of tetrakis (triphenylphosphine) palladium (0) to obtain 4'-(trans-4-n-pentyl-4-silacyclohexyl)-2-fluoro-4-methoxybiphenyl. This was then purified by means of chromatography to obtain 6.8 g of the target product (yield 92%).

[Example 13]

(Preparation of 4'-(trans-4-(3-methoxypropyl)-4-silacyclohexyl)-4-cyanobiphenyl )

6.5 g (20 mmol) of p-(trans-4-(3-methoxypropyl)-4-silacyclohexyl) bromobenzene was dripped into a mixture of 0. 5 g of magnesium (21 mmol) and 30 ml of THF to obtain a Grignard's reagent. This was dripped into a 20 ml THF solution of 2.8 g (20 mmol) of zinc chloride to obtain an organic zinc reagent. This solution was then dripped into a 50 ml THF solution of 4.6 g (20 mmol) of p-iodobenzonitrile and a catalytic amount of tetrakis (triphenylphosphine) palladium (0) to obtain 4'-(trans-4-(3-methoxypropyl)-4-silacyclohexyl)-4-cyanobiphenyl. This was then purified by means of chromatography to obtain 6.8 g of the target product (yield 98%).

[Example 14]

(Preparation of 4'-(trans-4-n-propyl-4-silacyclohexyl)-3,4-difluorobiphenyl)

3.0 g (20 mmol) of 1-chloro-3,4-difluorobenzene was dripped into a mixture of 0.5 g of magnesium (21 mmol) and 50 ml of THF to obtain a Grignard's reagent. This solution was then dripped into a 50 ml TMF solution of 6.9 g (20 mmol) of p-(trans-4-n-propyl-4-silacyclohexyl) iodobenzene and a catalytic amount of tetrakis (triphenylphosphine) palladium (0) to obtain 4'-(trans-4-n-propyl-4-silacyclohexyl)-3,4-difluorobiphenyl. This was then purified by means of chromatography to obtain 6.4 g of the target product (yield 97%). The results of its analysis are shown below.

IR (liquid film) vmax: 2918, 2873, 2100, 1605, 1504, 1311, 1119, 985, 889 and 812 $cm^{-1}$.

C-N transition temperature: 25.4° C.,
N-I transition temperature: 44.0° C.

[Example 15]

(Preparation of 4'-(trans-4-n-pentyl-4-silacyclohexyl)-4,2',6',-trifluorobiphenyl)

4.4 g (20 mmol) of p-iodofluorobenzene was dripped into a mixture of 0.5 g of magnesium (21 mmol) and 50 ml of THF to obtain a Grignard's reagent. This solution was then dripped into a 50 ml THF solution of 6.3 g (20 mmol) of 4-(trans-4 -n-pentyl-4-silacyclohexyl)-1-chloro-2,6-difluorobenzene and a catalytic amount of (1,3-bis (diphenylphosphino) propane) nickel chloride (II) to obtain 4'-(trans-4-n-pentyl-4-silacyclohexyl)-4,2',6',-trifluorobiphenyl. This was then purified by means of chromatography to obtain 7.8 g of the target product (yield 97%).

[Example 16]

(Preparation of 4'-(trans-4-n-pentyl-1-silacyclohexyl)-2,2'-difluoro-4-propylbiphenyl)

6.2 g (20 mmol) of 4-bromo-2,2'-difluoro-4'-propylbiphenyl was dripped into a mixture of 0.5 g of magnesium (21 mmol) and 50 ml of THF to obtain a Grignard's reagent. This solution was then dripped into a 50 ml THF solution of 4.0 g (20 mmol) of 4-n-pentyl-1-methoxy-1-silacyclohexane to obtain 4'-(trans-4-n-pentyl-1-silacyclohexyl)-2,2'-difluoro-4-propylbiphenyl. The silacyclohexane rings of this product were a mixture of trans isomers and cis isomers. They were separated by means of chromatography to obtain 6.4 g of the trans isomers (yield 80%).

[Example 17]

(Preparation of 4'-(trans-4-(3-methoxypropyl)-1-silacyclohexyl)-4-ethoxy-2-fluorobiphenyl)

5.9 g (20 mmol) of 4-bromo-2-fluoro-4-ethoxybiphenyl was dripped into a mixture of 0.5 g of magnesium (21 mmol)

and 50 ml of THF to obtain a Grignard's reagent. This solution was then dripped into a 50 ml THF solution of 4.1 g (20 mmol) of 4-(3-methoxypropyl)-1-chloro-1-silacyclohexane to obtain 4'-(trans-4-(8-methoxypropyl)-1-silacyclohexyl)-4-ethoxy-2-fluorobiphenyl. The silacyclohexane rings of this product were a mixture of trans and cis isomers. They were separated by means of chromatography to obtain 6.7 g of the trans isomer (yield 87%).

[Example 18]

(Preparation of 4'-(trans-4-n-pentyl-1-silacyclohexyl)-2'-fluoro-4-propylbiphenyl)

4.0 g (20 mmol) of p-propylbromobenzene was dripped into a mixture of 0.5 g of magnesium (21 mmol) and 50 ml of THF to obtain a Grignard's reagent. This solution was then dripped into a 50 ml THF solution of 6.0 g (20 mmol) of 1-chloro-2-fluoro-4-(trans-4-n-pentyl-1-silacyclohexyl) benzene and a catalytic amount of (1,3-bis (diphenylphosphino) propane) nickel chloride (II) to obtain 4'-(trans-4-n-pentyl-4-silacyclohexyl)-2'-fluoro-4-propylbiphenyl. This was then purified by means of chromatography to obtain 7.3 g of the target product (yield 95%).

[Example 19]

(Preparation of 4'-(trans-4-isobutyl-1-silacyclohexyl)-4-difluoromethoxybiphenyl)

3.6 g (20 mmol) of p-difluoromethoxychlorobenzene was dripped into a mixture of 0.5 g of magnesium (21 mmol) and 50 ml of THF to obtain a Grignard's reagent. This solution was then dripped into a 50 ml THF solution of 6.2 g (20 mmol) of p-(trans-4-isobutyl-1-silacyclohexyl) bromobenzene and a catalytic amount of tetrakis (triphenylphosphino) palladium (0) to obtain 4'-(trans-4-isobutyl-1-silacyclohexyl)-4-difluoromethoxybiphenyl. This was then purified by means of chromatography to obtain 7.0 g of the target product (yield 94%).

[Example 20]

(Preparation of 4' -(trans-4-n-pentyl-1-methyl-1-silacyclohexyl)-4-pentoxybiphenyl)

7.8 g (20 mmol) of p-(trans-4-n-pentyl-1-methyl-1-silacyclohexyl) iodobenzene was dripped into a mixture of 0.5 g of magnesium (21 mmol) and 50 ml of THF to obtain a Grignard's reagent. This solution was then dripped into a 50 ml THF solution of 4.9 g (20 mmol) of p-pentoxybromobenzene and a catalytic amount of tetrakis (triphenylphosphine) palladium (0) to obtain 4'-(trans-4-n-pentyl-1-methyl-1-silacyclohexyl)-4-pentoxybiphenyl. This was then purified by means of chromatography to obtain 7.7 g of the target product (yield 91%).

[Example 21]

(Preparation of 4'-(trans-4-n-pentyl-1-silacyclohexyl)-3,5-difluoro-4-difluoromethoxybiphenyl)

7.4 g (20 mmol) of p-(trans-4-n-pentyl-1-silacyclohexyl) iodobenzene was dripped into a mixture of 0.5 g of magnesium (21 mmol) and 50 ml of THF to obtain a Grignard's reagent. This solution was then dripped into a 50 ml THF solution of 6.1 g (20 mmol) of 3,5-difluoro-1-iodo-4-difluoromethoxybenzene and a catalytic amount of tetrakis (triphenylphosphine) palladium (0) to obtain 4'-(trans-4-n-pentyl-1-silacyclohexyl)-3,5-difluoro-4-difluoromethoxybiphenyl. This was then purified by means of chromatography to obtain 7.9 g of the target product (yield 93%).

[Example 22]

(Preparation of 4'-(trans-4-n-pentyl-1-silacyclohexyl)-3-fluoro-4-cyanobiphenyl)

6.5 g (20 mmol) of 4-(trans-4-n-pentyl-1-silacyclohexyl) bromobenzene was dripped into a mixture of 0.5 g of magnesium (21 mmol) and 30 ml of THF to obtain a Grignard's reagent. This was dripped into a 20 ml THF solution of 2.8 g (20 mmol) of zinc chloride to obtain an organic zinc reagent. This solution was then dripped into a 50 ml THF solution of 4.0 g (20 mmol) of 4-bromo-2-fluorobenzonitrile and a catalytic amount of tetrakis (triphenylphosphine) palladium (0) to obtain 4'-(trans-4-n-pentyl-1-silacyclohexyl)-S-fluoro-4-cyanobiphenyl. This was then purified by means of chromatography to obtain 6.9 g of the target product (yield 95%).

[Example 23]

(Preparation of 4'-(trans-4-n-pentyl-4-silacyclohexyl)-4-chloro-3-fluorobiphenyl)

6.5 g (20 mmol) of p-(trans-4-n-pentyl-4-silacyclohexyl) bromobenzene was dripped into a mixture of 0.5 g of magnesium (21 mmol) and 30 ml of THF to obtain a Grignard's reagent. This solution was then dripped into a 50 ml THF solution of 4.2 g (20 mmol) of 4-chloro-3-fluoro-1-bromobenzene and a catalytic amount of tetrakis (triphenylphosphine) palladium (0) to obtain 4'-(trans-4-n-pentyl-4-silacyclohexyl)-4-chloro-3-fluorobiphenyl. This was then purified by means of chromatography to obtain 6.8 g of the target product (yield 98%).

IR (liquid film) vmax: 2953, 2916, 2870, 2108, 1479, 1396, 1200, 985, 879 and 812 cm$^{-1}$ C-N transition temperature: 86.3° C.

N-I transition temperature: 103.5° C.

[Example 24]

(Preparation of 4'-(trans-4-n-propyl-1-methyl-1-silacyclohexyl)-4-cyanobiphenyl)

6.2 g (20 mmol) of 4-(trans-4-n-propyl-1-methyl-1-silacyclohexyl)- 1-bromobenzene was dripped into a mixture of 0.5 g of magnesium (21 mmol) and 80 ml of THF to obtain a Grignard's reagent. This was dripped into a 20 ml THF solution of 2.8 g (20 mmol) of zinc chloride to obtain an organic zinc reagent. This solution was then dripped into a 50 ml THF solution of 3.7 g (20 mmol) of 4-bromobenzonitrile and a catalytic amount of tetrakis (triphenylphosphine) palladium (0) to obtain 4'-(trans-4-n-propyl-1-methyl-1-silacyclohexyl)-4-cyanobiphenyl. This was then purified by means of chromatography to obtain 6.1 g of the target product (yield 91%).

IR (liquid film) vmax: 2956, 2912, 2839, 2224, 1606, 1254, 1113, 984, 854 and 806 cm$^{-1}$ C-I transition temperature: 87.0° C.

[Example 25]

(Preparation of 4'-(trans-4-n-butyl-1-methyl-1-silacyclohexyl)-4-cyanobiphenyl)

Preparation was conducted in the same manner as in Example 24 except for the fact that 4-(trans-4-n-butyl-1- methyl-1-silacyclohexyl)-1-bromobenzene was used instead of 4-(trans-4-n-propyl-1-methyl-1-silacyclohexyl)-1-bromobenzene to obtain 4'-(trans-4-n-butyl-1-methyl-1-silacyclohexyl)-4-cyanobiphenyl. This was then purified by means of chromatography to obtain 6.4 g of the target product (yield 92%).

IR (liquid film) vmax: 2956, 2918, 2858, 2839, 2229, 1608, 1242, 1115, 978, 850 and 812 cm$^{-1}$ C-I transition temperature: 78.2%

[Example 26]

(Preparation of 4'-(trans-4-n-pentyl-1-silacyclohexyl)-4-cyanobiphenyl)

Preparation was conducted in the same manner as in Example 24 except for the fact that 4-(trans-4-n-pentyl-1-silacyclohexyl)-1-bromobenzene was used instead of 4-(trans-4-n-propyl-1-methyl-1-silacyclohexyl)-1-bromobenzene to obtain 4'-(trans-4-n-pentyl-1-silacyclohexyl)-4-cyanobiphenyl. This was then purified by means of chromatography to obtain 6.0 g of the target product (yield 86%).

IR (liquid film) vmax: 2954, 2924, 2852, 2229, 2100, 1608, 1115, 985, 887, 850, 816, 814 and 808 cm$^{-1}$ C-S transition temperature: 79.1° C.

S-N transition temperature: 78.5° C. (monotropic)

N-I transition temperature: 114.3° C.

[Example 27]

(Preparation of 4'-(trans-4-ethyl-4-silacyclohexyl)-4-fluorobiphenyl)

3.5 g (20 mmol) of p-fluorobromobenzene was dripped into a mixture of 0.5 g of magnesium (21 mmol) and 50 ml of THF to obtain a Grignard's reagent. This solution was then dripped into a 50 ml THF solution of 5.7 g (20 mmol) of 4-(trans-4 -ethyl-4-silacyclohexyl) bromobenzene and a catalytic amount of tetrakis (triphenylphosphine) palladium (0) to obtain 4'-(trans-4-ethyl-4-silacyclohexyl)-4-fluorobiphenyl. This was then purified by means of chromatography to obtain 5.6 g of the target product (yield 94%).

IR (liquid film) vmax: 2956, 2916, 2873, 2096, 1495, 1238, 966, 887, 881 and 814 cm$^{-1}$ C-N transition temperature: 94.5° C.

N-I transition temperature: 95.8%

[Example 28]

(Preparation of 4'-(trans-4-n-pentyl-4-silacyclohexyl)-4-fluorobiphenyl)

Preparation was conducted in the same manner as in Example 27 except for the fact that 4-(trans-4-n-pentyl-4-silacyclohexyl) bromobenzene was used instead of 4-(trans-4-ethyl-4-silacyclohexyl) bromobenzene to obtain 4'-(trans-4-n-pentyl-4-silacyclohexyl)-4-fluorobiphenyl. This was then purified by means of chromatography to obtain 6.3 g of the target product (yield 93%).

IR (liquid film) vmax: 2916, 2852, 2096, 1495, 1238, 982, 883, 835 and 810 cm$^{-1}$ C-N transition temperature: 70.8%

N-I transition temperature: 117.8%

[Example 29]

(Preparation of 4'-(trans-4-(3-methylbutyl)-4-silacyclohexyl)-3,4-difluorobiphenyl)

2.5 g (20 mmol) of 3-methylbutyl bromide was dripped into a mixture of 0.5 g of magnesium (21 mmol) and 50 ml of THF to obtain a Grignard's reagent. This solution was then dripped into a 50 ml THF solution of 6.5 g (21 mmol) of 4'-(4-chloro-4-silacyclohexyl)-3,4-difluorobiphenyl to obtain 4'-(trans-4-(3-methylbutyl)-4-silacyclohexyl)-3,4-difluorobiphenyl. The silacyclohexane rings of this product were a mixture of trans and cis isomers. They were separated by means of chromatography to obtain 6.5 g of the trans isomer (yield 90%). The results of its analysis are shown below.

IR (liquid film) vmax: 2956, 2914, 2872, 2846, 2108, 1603, 1527, 1506, 1497, 1269, 1184, 987, 893, 889 and 816 cm$^{-1}$ C-N transition temperature: 64.3° C.

N-I transition temperature: 32.6° C. (monotropic)

[Example 30]

(Preparation of 4'-(trans-4-(3-methoxypropyl)-4-silacyclohexyl)-3,4-difluorobiphenyl)

Preparation was conducted in the same manner as in Example 29 except for the fact that 3-methoxypropyl bromide was used instead of 3-methylbutyl bromide to obtain 4'-(trans-4-(3-methoxypropyl)-4-silacyclohexyl)-3,4-difluorobiphenyl. This was then purified by means of chromatography to obtain 6.3 g of the target product (yield 93%).

IR (liquid film) vmax: 2908, 2906, 2850, 2098, 1605, 1529, 1265, 1184, 1109, 984, 885, 877 and 810 cm$^{-1}$ C-N transition temperature: 58.3%

N-I transition temperature: 60.1° C.

[Example 31]

(Preparation of 4'-(trans-4-(4-pentenyl)-4-silacyclohexyl)-3,4-difluorobiphenyl)

Preparation was conducted in the same manner as in Example 29 except for the fact that 4-pentenyl bromide was used instead of 3-methylbutyl bromide to obtain 4'-(trans-4-(4-pentenyl)-4-silacyclohexyl)-3,4-difluorobiphenyl. This was then purified by means of chromatography to obtain 6.3 g of the target product (yield 93%).

IR (liquid film) vmax: 2918, 2850, 2108, 1608, 1527, 1510, 508, 1506, 1404, 1269, 985, 877 and 812 cm$^{-1}$ C-N transition temperature: 34.6° C.

N-I transition temperature: 32.4° C. (monotropic)

[Example 32]

(Preparation of 4'-(trans-4-ethyl-4-silacyclohexyl)-3,4-difluorobiphenyl)

3.9 g (20 mmol) of 3,4-difluorobromobenzene was dripped into a mixture of 0.5 g of magnesium (21 mmol) and 50 ml of THF to obtain a Grignard's reagent. This solution was then dripped into a 50 ml THF solution of 5.7 g (20 mmol) of 4-(trans-4-ethyl-4-silacyclohexyl) bromobenzene and a catalytic amount of tetrakis (triphenylphosphine) palladium (0) to obtain 4'-(trans-4-ethyl-4-silacyclohexyl)-3,4-difluorobiphenyl. This was then purified by means of chromatography to obtain 6.1 g of the target product (yield 88%).

IR (liquid film) vmax: 2927, 2924, 2877, 2110, 1603, 1531, 1506, 1402, 1120, 987, 887, 879 and 808 cm$^{-1}$ C-N transition temperature: 39.0° C.

N-I transition temperature: 37.8° C. (monotropic)

[Example 33]

(Preparation of 4'-(trans-4-n-propyl-4-methyl-4-silacyclohexyl)-3,4-difluorobiphenyl)

Preparation was conducted in the same manner as in Example 32 except for the fact that 4-(trans-4-n-propyl-4- methyl-4-silacyclohexyl) bromobenzene was used instead of 4-(trans-4-ethyl-4-silacyclohexyl) bromobenzene to obtain 4'-(trans-4-n-propyl-4-methyl-4-silacyclohexyl)-3,4-difluorobiphenyl. This was then purified by means of chromatography to obtain 6.6 g of the target product (yield 96%).

IR (liquid film) vmax: 2956, 2918, 2873, 2100, 1529, 1504, 1404, 1119, 985, 889, 877 and 812 cm$^{-1}$ C-I transition temperature: 62.0° C.

[Example 34]

(Preparation of 4'-(trans-4-n-pentyl-4-silacyclohexyl)-3,4-difluorobiphenyl)

Preparation was conducted in the same manner as in Example 32 except for the fact that 4-(trans-4-n-pentyl-4-silacyclohexyl) bromobenzene was used instead of 4-(trans-4-ethyl-4-silacyclohexyl) bromobenzene to obtain 4'-(trans-4-n-pentyl-4-silacyclohexyl)-3,4-difluorobiphenyl. This was then purified by means of chromatography to obtain 6.4 g of the target product (yield 90%).

IR (liquid film) vmax: 2958, 2916, 2850, 2108, 1605, 1527, 1506, 1269, 985, 879, 881 and 812 cm$^{-1}$ C-N transition temperature: 48.1° C.

N-I transition temperature: 63.8° C.

[Example 35]

(Preparation of 4'-(trans-4-n-pentyl-4-silacyclohexyl)-3,4,2',6'-tetrafluorobiphenyl)

Preparation was conducted in the same manner as in Example 32 except for the fact that 2,6-difluoro-4-(trans-4-n-pentyl-4-silacyclohexyl)-1-bromobenzene was used instead of 4-(trans-4-ethyl-4-silacyclohexyl) bromobenzene to obtain 4'-(trans-4-n-pentyl-4-silacyclohexyl)-3,4,2',6'-tetrafluorobiphenyl. This was then purified by means of chromatography to obtain 6.7 g of the target product (yield 85%).

IR (liquid film) vmax: 2954, 2918, 2845, 2110, 1639, 1491, 1410, 1200, 1119, 1018, 885 and 818 cm$^{-1}$ C-I transition temperature: 63.1° C.

[Example 36]

(Preparation of 4'-(trans-4-n-pentyl-4-silacyclohexyl)-3,4,5,2'-tetrafluorobiphenyl)

Preparation was conducted in the same manner as in Example 32 except for the fact that 2-fluoro-4-(trans-4-n-pentyl-4-silacyclohexyl)-1-bromobenzene was used instead of 4-(trans-4-ethyl-4-silacyclohexyl)-1-bromobenzene and that 3,4,5-trifhorobromobenzene was used instead of 3,4-difluorobromobenzene to obtain 4'-(trans-4-n-pentyl-4-silacyclohexyl)-3,4,5,2'-tetrafluorobiphenyl. This was then purified by means of chromatography to obtain 6.5 g of the target product (yield 83%).

IR (liquid film) vmax: 2956, 2920, 2854, 2102, 1618, 1537, 1502, 1406, 1120, 1047, 989, 889, 864 and 818 cm$^{-1}$ C-N transition temperature: 23.7° C.

N-I transition temperature: 3.8° C. (monotropic)

[Example 37]

(Preparation of 4'-(trans-4-propyl-1-methyl-1-silacyclohexyl)-4-trifluoromethoxybiphenyl)

6.2 g (20 mmol) of 4'-(trans-4-propyl-1-methyl-1-silacyclohexyl) bromobenzene was dripped into a mixture of 0.5 g of magnesium (21 mmol) and 50 ml of THF to obtain a Grignard's reagent. This solution was then dripped into a 50 ml THF solution of 4.8 g (20 mmol) of p-trifluoromethoxybromobenzene and a catalytic amount of tetrakis (triphenylphosphine) palladium (0) to obtain 4'-(trans-4-propyl-1-methyl-1-silacyclohexyl)-4-trifluoromethoxybiphenyl. This was then purified by means of chromatography to obtain 6.8 g of the target product (yield 87%).

IR (liquid film) vmax: 2956, 2910, 2848, 1518, 1489, 1259, 1221, 1167, 1115 and 804 cm$^{-1}$ C-I transition temperature: lower than –50° C.

[Example 38]

(Preparation of 4'-(trans-4-n-pentyl-4-silacyclohexyl)-2'-fluoro-4-trifluoromethoxybiphenyl)

3.0 g (20 mmol) of n-pentyl bromide was dripped into a mixture of 0.5 g of magnesium (21 mmol) and 50 ml of THF to obtain a Grignard's reagent. This solution was then dripped into a 50 ml THF solution of 7.8 g (21 mmol) of 4'-(4-chloro-4-silacyclohexyl)-2'-fluoro-4-trifluoromethoxybiphenyl to obtain 4'-(trans-4-n-pentyl-4-silacyclohexyl)-2'-fluoro-4-trifluoromethoxybiphenyl. The silacyclohexane rings of this product were a mixture of trans and cis isomers. They were separated by means of chromatography to obtain 6.8 g of the trans isomer (yield 80%).

IR (liquid film) vmax: 2958, 2950, 2854, 2104, 1624, 1493, 1259, 1213, 1169, 989, 858 and 818 cm$^{-1}$ C-S transition temperature: 38.9%

S-N transition temperature: –2.0° C. (monotropic)

N-I transition temperature: 72.2° C.

[Example 39]

(Preparation of 4'-(trans-4-n-pentyl-4-silacyclohexyl)-3-fluoro-4-difluoromethoxybiphenyl)

3.0 g (20 mmol) of n-pentyl bromide was dripped into a mixture of 0.5 g of magnesium (21 mmol) and 50 ml of THF to obtain a Grignard's reagent. This solution was then dripped into a 50 ml THF solution of 7.4 g (20 mmol) of 4'-(4-chloro-4-silacyclohexyl)-3-fluoro-4-difluoromethoxybiphenyl to obtain 4'-(trans-4-n-pentyl-4-silacyclohexyl)-3-fluoro-4-difluoromethoxybiphenyl. The silacyclohexane rings of this product were a mixture of trans and cis isomers. They were separated by means of chromatography to obtain 6.6 g of the trans isomer (yield 81%).

IR (liquid film) vmax: 2956, 2920, 2852, 2100, 1593, 1500, 1402, 1142, 1113, 1061, 987, 887, 879 and 812 cm$^{-1}$ C-S transition temperature: 21.3° C.

S-N transition temperature: 30.8° C.

N-I transition temperature: 83.5° C.

[Example 40]

(Preparation of 4'-(trans-4-n-propyl-4-silacyclohexyl)-3-fluoro-4-difluoromethoxybiphenyl)

Preparation was conducted in the same manner as in Example 39 except for the fact that n-propyl bromide was used instead of n-pentyl bromide to obtain 4'-(trans-4-n-propyl-4-silacyclohexyl)-3-fluoro-4-difluoromethoxybiphenyl. The silacyclohexane rings of this product were a mixture of trans isomers and cis isomers.

They were separated by means of chromatography to obtain 6.1 g of the trans isomers (yield 80%).

IR (liquid film) vmax: 2956, 2918, 2102, 1593, 1500, 1402, 1140, 1111, 1063, 889 and 814 cm$^{-1}$ C-S transition temperature: 33.9%

S-N transition temperature: 33.0% (monotropic)

N-I transition temperature: 86.6%

[Example 41]

(Preparation of 4'-(trans-4-n-pentyl-4-silacyclohexyl)-3,5-difluoro-4-difluoromethoxybiphenyl)

3.0 g (20 mmol) of n-pentyl bromide was dripped into a mixture of 0.5 g of magnesium (21 mmol) and 50 ml of THF to obtain a Grignard's reagent. This solution was then dripped into a 50 ml THF solution of 7.8 g (20 mmol) of 4'-(4-chloro-4-silacyclohexyl)-3,5-difluoro-4-difluoromethoxybiphenyl to obtain 4'-(trans-4-n-pentyl-4-silacyclohexyl)-3,5-difluoro- 4-difluoromethoxybiphenyl. The silacyclohexane rings of this product were a mixture of trans and cis isomers. They were separated by means of chromatography to obtain 6.6 g of the trans isomer (yield 82%).

IR (liquid film) vmax: 2920, 2852, 2102, 1601, 1502, 1381, 1362, 1230, 1146, 1101, 1038, 877 and 822 cm$^{-1}$ C-S transition temperature: 23.5%

N-I transition temperature: 47.7° C.

[Example 42]

(Preparation of 4'-(trans-4-n-propyl-4-silacyclohexyl)-3,5-difluoro-4-difluoromethoxybiphenyl)

Preparation was conducted in the same manner as in Example 41 except for the fact that n-propyl bromide was used instead of n-pentyl bromide to obtain 4'-(trans-4-n-propyl-4-silacyclohexyl)-3,5-difluoro-4-difluoromethoxybiphenyl. The silacyclohexane rings of this product were a mixture of trans and cis isomers. They were separated by means of chromatography to obtain 6.3 g of the trans isomer (yield 80%).

IR (liquid film) vmax: 2904, 2846, 2104, 1599, 1502, 1404, 1362, 1230, 1115, 1063, 876 and 814 cm$^{-1}$ C-S transition temperature: 43.1° C.

N-I transition temperature: 45.5° C.

[Example 43]

(Preparation of 4'-(trans-4-n-propyl-4-silacyclohexyl)-2'-fluoro-4-trifluoromethoxybiphenyl)

Preparation was conducted in the same manner as in Example 38 except for the fact that n-propyl bromide was used instead of n-pentyl bromide to obtain 4'-(trans-4-n-propyl-4-silacyclohexyl)-2'-fluoro-4-trifluoromethoxybiphenyl. The silacyclohexane rings of this product were a mixture of trans and cis isomers. They were separated by means of chromatography to obtain 6.4 g of the trans isomer (yield 81%).

IR (KBr disc) vmax: 2958, 2924, 2848, 2114, 1624, 1589, 1493, 1273, 1209, 1163, 989, 889 and 825 cm$^{-1}$ C-N transition temperature: 57.7° C.

N-I transition temperature: 81.9° C.

[Example 44]

(Preparation of 4'-(trans-4-n-propyl-4-silacyclohexyl)-2',4-difluorobiphenyl)

2.5 g (20 mmol) of n-propyl bromide was dripped into a mixture of 0.5 g of magnesium (21 mmol) and 50 ml of THF to obtain a Grignard's reagent. This solution was then dripped into a 50 ml THF solution of 7.8 g (20 mmol) of 4'-(4-chloro-4-silacyclohexyl)-3,5-difluoro-4-difluoromethoxybiphenyl to obtain 4'-(trans-4-n-propyl-4-silacyclohexyl)-2',4-difluorobiphenyl. The silacyclohexane rings of this product were a mixture of trans and cis isomers. They were separated by means of chromatography to obtain 5.4 g of the trans isomer (yield 82%).

IR (KBr disc) vmax: 2958, 2918, 2845, 2108, 1603, 1489, 1400, 1225, 1122, 985, 887, 841 and 825 cm$^{-1}$ C-N transition temperature: 69.2° C.

N-I transition temperature: 71.1%

[Example 45]

(Preparation of 4'-(trans-4-n-pentyl-4-silacyclohexyl)-2',4-difluorobiphenyl)

Preparation was conducted in the same manner as in Example 44 except for the fact that n-pentyl bromide was used instead of n-propyl bromide to obtain 4'-(trans-4-n-pentyl-4-silacyclohexyl)-2',4-difluorobiphenyl. The silacyclohexane rings of this product were a mixture of trans and cis isomers. They were separated by means of chromatography to obtain 5.7 g of the trans isomer (yield 80%).

IR (KBr disc) vmax: 2956, 2918, 2846, 2104, 1603, 1489, 1406, 1225, 1122, 987, 887, 845 and 823 cm$^{-1}$ C-N transition temperature: 57.7° C.

N-I transition temperature: 81.9° C.

[Example 46]

(Preparation of 4'-(trans-4-(4-fluorobutyl)-4-silacyclohexyl)-4-trifluoromethoxybiphenyl)

3.1 g (20 mmol) of fluorobutyl bromide was dripped into a mixture of 0.5 g of magnesium (21 mmol) and 50 ml of THF to obtain a Grignard's reagent. This solution was then dripped into a 50 ml THF solution of 7.4 g (20 mmol) of 4'-(4-chloro-4-silacyclohexyl)-4-trifluoromethoxybiphenyl to obtain 4'-(trans-4-(4-fluorobutyl)-4-silacyclohexyl)-4-trifluoromethoxybiphenyl. The silacyclohexane rings of this product were a mixture of trans isomers and cis isomers. They were separated by means of chromatography to obtain 5.8 g of the trans isomers (yield 71%).

[Example 47]

(Preparation of 4'-(trans-4-(4-fluoropentyl)-4-silacyclohexyl)-3,4-difluorobiphenyl)

3.4 g (20 mmol) of fluoropentyl bromide was dripped into a mixture of 0.5 g of magnesium (21 mmol) and 50 ml of THF to obtain a Grignard's reagent. This solution was then dripped into a 50 ml THF solution of 6.5 g (20 mmol) of 4'-(4-chloro-4-silacyclohexyl)-3,4-difluorobiphenyl to obtain 4'-(trans-4-(4-fluorobutyl)-4-silacyclohexyl)-3,4-difluorobiphenyl. The silacyclohexane rings of this product were a mixture of trans isomers and cis isomers. They were separated by means of chromatography to obtain 6.3 g of the trans isomers (yield 74%).

[Example 48]

(Preparation of 4'-(trans-4-n-pentyl-4-silacyclohexyl)-2,3-difluoro-4-ethoxybiphenyl)

Preparation was conducted in the same manner as in Example 38 except for the fact that 4'-(4-chloro -4-silacyclohexyl)-2,3-difluoro-4-ethoxybiphenyl was used instead of 4'-(4-chloro-4-silacyclohexyl)-2'-fluoro-4-trifluoromethoxybiphenyl to obtain 4'-(trans-4-n-pentyl-4-silacyclohexyl)-2,3-difluoro-4-ethoxybiphenyl. The silacyclohexane rings of this product were a mixture of trans and cis isomers. They were separated by means of chromatography to obtain 6.8 g of the trans isomer (yield 85%).

IR (KBr disc) vmax: 2920, 2899, 2846, 2112, 1502, 1473, 1315, 1296, 1145, 1076, 879 and 818 cm$^{-1}$ C-N transition temperature: 74.7° C.

N-I transition temperature: 139.1° C.

[Example 49]

(Preparation of 4'-(trans-4-n-pentyl-4-silacyclohexyl)-4-chloro-3,5-difluorobiphenyl)

Preparation was conducted in the same manner as in Example 38 except for the fact that 4'-(4-chloro-4-silacyclohexyl)-4-chloro-3,5-difluorobiphenyl was used instead of 4'-(4-chloro-4-silacyclohexyl)-2'-fluoro-4-trifluoromethoxybiphenyl to obtain 4'-(trans-4-n-pentyl-4-silacyclohexyl)-4-chloro-3,5-difluorobiphenyl. The silacyclohexane rings of this product were a mixture of trans and cis isomers. They were separated by means of chromatography to obtain 6.3 g of the trans isomer (yield 80%).

IR (KBr disc) vmax: 2916, 2846, 2102, 1639, 1578, 1437, 1396, 1198, 1093, 1018, 887, 831 and 816 cm$^{-1}$ C-N transition temperature: 75.0%

N-I transition temperature: 69.0° C. (monotropic)

[Example 50]

(Preparation of 4'-(trans-4-n-pentyl-4-silacyclohexyl)-2',6'-difluoro-4-trifluoromethoxybiphenyl)

Preparation was conducted in the same manner as in Example 38 except for the fact that 4'-(4-chloro-4-silacyclohexyl)-2',6'-difluoro-4-trifluoromethoxybiphenyl was used instead of 4'-(4-chloro-4-silacyclohexyl)-2'-fluoro-4-trifluoromethoxybiphenyl to obtain 4'-(trans-4-n-pentyl-4-silacyclohexyl)-2',6'-difluoro-4-trifluoromethoxybiphenyl. The silacyclohexane rings of this product were a mixture of trans and cis isomers. They were separated by means of chromatography to obtain 7.3 g of the trans isomer (yield 81%).

IR (KBr disc) vmax: 2958, 2920, 2852, 2127, 1637, 1566, 1431, 1269, 1227, 1157, 1018, 889, 850 and 816 cm$^{-1}$ C-I transition temperature: 62.7° C.

[Example 51]

Mixture A comprising 43 mole % of trans-4-(2-(trans-4-(3,4-difluorophenyl)cyclohexyl)ethyl)-1-ethyl-1-silacyclohexane, 17 mole % of trans-4-(2-(trans-4-(3,4-difluorophenyl)cyclohexyl)ethyl)-1-n-propyl-1-silacyclohexane and 40 mole % of trans-4-(2-(trans-4-(3,4-difluorophenyl)cyclohexyl)ethyl)-1-n-pentyl-1-silacyclohexane exhibited the following characteristics:

C-N transition temperature: -10.7° C.
N-I transition temperature: 93.8° C.
Threshold voltage (5 micrometer-cell, 32 Hz): 2.5 V
Refractive index anisotropy delta-n (589 nm): 0.0720

A mixture comprising 85 mole % of this mixture A and 15 mole % of 4'-(trans-4-n-pentyl-4-silacyclohexyl)-2'-fluoro-4-trifluoromethoxybiphenyl obtained in Example 38 exhibited the following characteristics:

C-N transition temperature: -16.1° C.
N-I transition temperature: 90.6° C.
Threshold voltage (5 micrometer-cell, 32 Hz): 2.20 V
Refractive index anisotropy delta-n (589 nm): 0.0809

As described above, the addition of the compound of this invention allowed extension of the nematic phase into a low temperature region, leading to higher flowability (low viscosity) at low temperatures, an increase in the refractive index anisotropy and a reduction of the threshold voltage.

The liquid crystal compounds of this invention which have Si as a ring composing element have the effect of increasing the refractive index anisotropy as well as the following advantages over liquid crystal compounds which have a conventional BCH structure comprising similar hydrocarbon rings:

(1) Since the nematic liquid crystal phase extends to low temperatures, the low temperature features which follow are improved:

(2) Viscosity in a low temperature range drops, resulting in an improved response time in the low temperature range.

(3) Compatibility in a low temperature range improves.

Also, liquid crystal compounds whose X in the general formula (I) is neither R nor OR have, in addition to the advantages mentioned above, an effect of lowering the threshold voltage because of a greater dielectric anisotropy.

The liquid crystal compounds of this invention, depending on the selection of substitutional groups in the composition, can be widely used as the base material which comprises the major component of the liquid crystal phase, in a manner similar to how the conventional liquid crystal compounds with a BCH structure of similar hydrocarbon rings are used.

The liquid crystal compound whose substitutional group X in the general formula (I) is R or OR has near-zero dielectric anisotropy, and therefore it should preferably be used for the liquid crystal phase for display based on the dynamic scattering (DS) or deformation of aligned phase (DAP mode). The compounds in which X is other than R or OR should preferably be used for manufacturing the liquid crystal phase with a large positive dielectric anisotropy which is used in display elements based on the twisted nematic cell or the cholesteric-nematic phase transition.

We claim:

1. A silacyclohexane compound represented by the following formula (I):

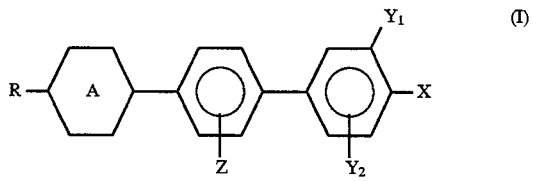

wherein R denotes a linear-chain alkyl group with a carbon number of 1–10, a mono- or di- fluoro-alkyl group with a carbon number of 1–10, a branched-chain alkyl group with a carbon number of 3–8, an alkoxyalkyl group with a carbon number of 2–7, or an alkenyl group with a carbon number of 2–8, and

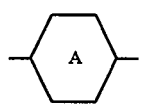

denotes a trans-1-sila-1,4-cyclohexylene or a trans-4-sila-1,4-cyclohexylene group whose silicon at position 1 or position 4 has a substitutional group(s) of H, F, Cl or $CH_3$, X denotes CN, F, Cl, $CF_3$, $CF_2Cl$, $CHFCl$, $OCF_3$, $OCHFCl_2$, $OCHFCl$, R or OR group; wherein R is the same as defined in formula (I); $Y_2$ and Z denote H or F, independently to each other, and $Y_1$ denotes H, F or Cl.

2. A method of preparing the silacyclohexane compound as described in claim 1, by reacting an organometallic reagent R-M, whereby R is the same as defined in formula (I), M denotes MgP, ZnP; and P denotes a halogen atom or Li; with a silacyclohexane compound

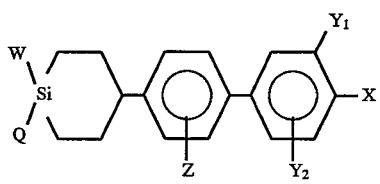

wherein W denotes a H, F, Cl or $CH_3$ group, Q denotes a halogen or alkoxy group, and X, $Y_1$, $Y_2$ and Z are the same as defined in formula (I).

3. A method of preparing the silacyclohexane compound as described in claim 1 by reacting an organometallic reagent

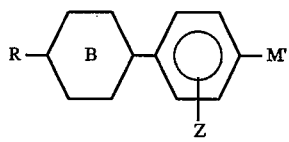

wherein R and Z are the same as defined in formula (I) in claim 1, M' denotes M, or $B(OR')_2$; R' denotes a Me group or an H atom, and

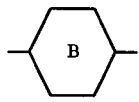

denotes a trans-1-sila-1,4-cyclohexylene or trans-4-sila-1,4-cyclohexylene group whose silicon at position 1 or position 4 has a substitutional group(s) of H or $CH_3$, with an aromatic compound

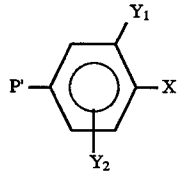

wherein $P^1$ denotes Cl, Br of I, and X, $Y_1$ and $Y_2$ are the same as defined in formula (I).

4. A method of preparing the silacyclohexane compound as described in claim 1 by reacting an organometallic reagent

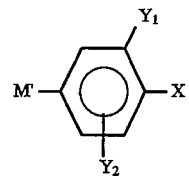

wherein X, $Y_1$ and $Y_2$ are the same as defined in formula (I), and M', denotes M, or $B(OR')_2$; M is MgP, ZnP, and P is a halogen atom or Li, R' renotes a Me or an H atom, with a silacyclohexane compound

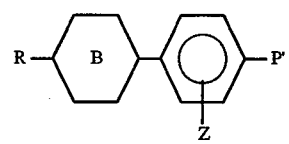

wherein R and Z are the same as defined in claim 1, $P^1$ denotes Cl, Br or I, and

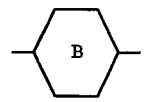

denotes a trans-1-sila-1,4-cyclohexylene or trans-4-sila-1,4-cyclohexylene group whose silicon at position 1 or position 4 has a substitutional group(s) of H or $CH_3$.

5. A method of preparing the silacyclohexane compound as described in claim 1 by reacting a silacyclohexane compound

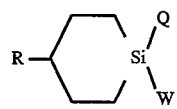

wherein R is the same as defined in claim 1, and W denotes H, F, Cl or $CH_3$, Q denotes a halogen or alkoxy group, with an organometallic reagent

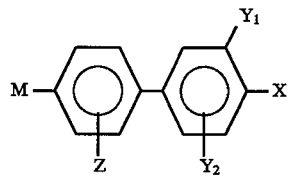

wherein X, $Y_1$ and Z are the same as defined in formula (I) in claim 1, M denotes MgP ZnP, and P denotes a halogen atom or Li.

6. A liquid crystal composition comprising the compound described in claim 1.

* * * * *